(12) United States Patent
Heuer et al.

(10) Patent No.: US 7,132,497 B2
(45) Date of Patent: Nov. 7, 2006

(54) AROMATIC DIHYDROXY COMPOUND USEFUL FOR THE PREPARATION OF (CO)POLYCARBONATES

(75) Inventors: Helmut-Werner Heuer, Krefeld (DE); Rolf Wehrmann, Krefeld (DE)

(73) Assignee: Bayer Materialscience Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/921,390

(22) Filed: Aug. 19, 2004

(65) Prior Publication Data

US 2005/0054808 A1  Mar. 10, 2005

(30) Foreign Application Priority Data

Aug. 23, 2003  (DE) ................ 103 38 907

(51) Int. Cl.
    *C08G 63/00* (2006.01)
(52) U.S. Cl. ............ 528/190; 264/176.1; 264/219; 528/176; 528/193; 528/194; 528/196; 528/198; 568/838
(58) Field of Classification Search ............ 264/176.1, 264/219; 528/176, 190, 196, 198; 518/193, 518/194; 568/838
    See application file for complete search history.

(56) References Cited

U.S. PATENT DOCUMENTS

| 3,220,977 A | 11/1965 | Jackson, Jr. et al. ......... 260/47 |
| 4,520,187 A | 5/1985 | Mark et al. ................ 528/176 |
| 5,378,570 A | 1/1995 | Kobayashi et al. ........... 430/58 |

FOREIGN PATENT DOCUMENTS

EP    DE 4001932    *  7/1991

OTHER PUBLICATIONS

Tetrahedron Lett., vol. 34, No. 19, (month unavailable) 1993, pp. 3075-3078, Lissa A Fowley et al, "Colloidal Palladium, Easily Formed in Organic Solvents, is a Highly Active and Stable Catalyst for Selective Hydrogenations and Dehydrohalogenations".
Helvetica Chimica Acta, vol. 76(5), (month unavailable) 1993, pp. 2070-2088, Christian Chapuis et al, Preparation of Optically Active Flowery and Woody-Like Odorant Ketones.
*Via Corey-Chaykovsky* Oxiranylation: Irones and Analogues.
Patent Abstracts of Japan Bd. 2003, Nr. 10, Oct. 8, 2003 & JP 2003 178489 A Hitachi Maxell Ltd), Jun. 27, 2003 Zusammanfassung -& JP 2003 178489 A (Hitachi Maxell Ltd) Jun. 27, 2003 Anspruch 5; Tabelle 2; Verbindung 5.
Patent Abstracts of Japan Bd. 2000, Nr 12, Jan. 3, 2001 & JP 2000 265075 A Teijin Chem Ltd), Sep. 26, 2000 Zusammenfassung & JP 2000 265075 A (Teijin Chem Ltd) Sep. 26, 2000 Formel I.
Patent Abstracts of Japan Bd. 1999, Nr. 11, Sep. 30, 1999 & JP 11 149166 A (Fuji Xerox Co Ltd) Jun. 2, 1999 Tabellen und Formeln I, II, II, IV & VII.
Patent Abstracts of Japan Bd. 018, Nr. 228 (P-1730), Apr. 25, 1994 & JP 06 019167 A (Canon Inc), Jan. 28, 1994 Zusammenfassung & JP 06 019167 A (Canon Inc) Jan. 28, 1994 Polymere P-1, P-6, P-7, P-11, P-16, P-17.

* cited by examiner

*Primary Examiner*—Terressa Boykin
(74) *Attorney, Agent, or Firm*—Joseph C. Gil; Aron Preis

(57) ABSTRACT

An aromatic dihydroxy compound conforming to formula 1

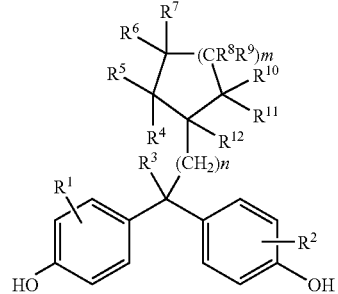

(1)

is disclosed. Also disclosed are (co)polycarbonates derived from the compound. The novel (co)polycarbonates are characterized by their reduced water uptake and improved flowability.

7 Claims, No Drawings

AROMATIC DIHYDROXY COMPOUND USEFUL FOR THE PREPARATION OF (CO)POLYCARBONATES

FIELD OF THE INVENTION

The invention relates to an aromatic dihydroxy compound and to its use in the preparation of thermoplastic (co) polycarbonate.

SUMMARY OF THE INVENTION

An aromatic dihydroxy compound conforming to formula 1

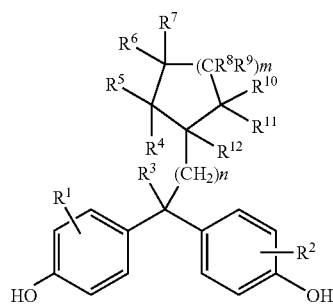

(1)

is disclosed. Also disclosed are (co)polycarbonates derived from the compound. The novel (co)polycarbonates are characterized by their reduced water uptake and improved flowability.

BACKGROUND OF THE INVENTION

The present invention provides polycarbonates and copolycarbonates of reduced water uptake and improved flowability, processes for their preparation and their use for the production of particular products and the products obtainable therefrom. The invention furthermore provides new bisphenols and processes for their preparation and their use.

Aromatic polycarbonates belong to the group of industrial thermoplastics. They are distinguished by the combination of the technologically important properties of transparency, heat resistance and toughness.

To obtain high molecular weight polycarbonates by the phase boundary process, the alkali metal salts of bisphenols are reacted with phosgene in the two-phase mixture. The molecular weight may be controlled by the amount of monophenols, such as e.g. phenol or tert-butylphenol. Practically exclusively linear polymers are formed in these reactions. This may be demonstrated by end group analysis. Branched polycarbonates are also obtained in this reaction by the controlled use of so-called branching agents, as a rule polyhydroxylated compounds.

For the preparation of polycarbonates by the phase boundary process, reference may be made by way of example to H. Schnell, Chemistry and Physics of Polycarbonates, Polymer Reviews, vol. 9, Interscience Publishers, New York 1964 p. 33 et seq. and to Polymer Reviews, vol. 10, "Condensation Polymers by Interfacial and Solution Methods", Paul W. Morgan, Interscience Publishers, New York 1965, chap. VIII, p. 325.

For the preparation of polycarbonates by the melt transesterification process, the bisphenols are reacted with diaryl carbonates, usually diphenyl carbonate, in the presence of catalysts, such as alkali metal salts or ammonium or phosphonium compounds, in the melt.

The melt transesterification process is described, for example, in the Encyclopedia of Polymer Science, vol. 10 (1969), Chemistry and Physics of Polycarbonates, Polymer Reviews, H. Schnell, vol. 9, John Wiley and Sons, Inc. (1964) and DE-C 10 31 512.

However, the polycarbonates and copolycarbonates already described in the prior art are unsatisfactory due to their water uptake and the limited dimensional stability thereby caused, or have the disadvantage that when used as data carrier materials they may be of limited or non-optimum suitability at reading wavelengths in the blue or blue-green range.

DETAILED DESCRIPTION OF THE INVENTION

There was therefore the object of providing polycarbonates and copolycarbonates and processes for their preparation which avoid these disadvantages. This object is achieved, surprisingly, by the use of the aromatic dihydroxy compound (herein bisphenol) according to the invention, of the general formula (1)

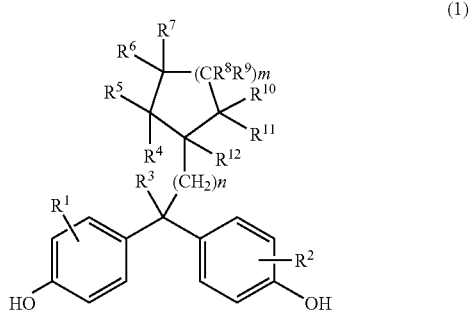

(1)

in which $R^1$ and $R^2$ independently one of the other represent hydrogen or linear or branched $C_1$–$C_{10}$ alkyl, preferably hydrogen or linear or branched $C_1$–$C_6$ alkyl, particularly preferably hydrogen or linear or branched $C_1$–$C_4$ alkyl, very particularly preferably hydrogen or $C_1$-alkyl, $R^3$ represents hydrogen or linear or branched $C_1$–$C_{10}$ alkyl, preferably linear or branched $C_1$–$C_{10}$ alkyl, preferably linear or branched $C_1$–$C_6$ alkyl, particularly preferably linear or branched $C_1$–$C_4$ alkyl, very particularly preferably $C_1$-alkyl, $R^4$ to $R^{12}$ independently represent hydrogen or linear or branched $C_1$–$C_{10}$ alkyl, preferably hydrogen or linear or branched $C_1$–$C_6$ alkyl, particularly preferably hydrogen or linear or branched $C_1$–$C_4$ alkyl, very particularly preferably hydrogen or $C_1$-alkyl and n and m independently of one another represent an integer of 0 to 10, preferably 1 to 8, particularly preferably 1 to 6, very particularly preferably 2 to 4.

The bisphenol according to the invention is particularly preferably described by the general formula (2)

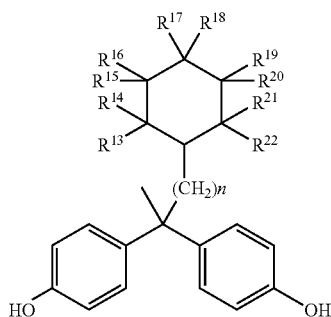

(2)

in which
R$^{13}$ to R$^{22}$ independently represents hydrogen or linear or branched C$_1$–C$_4$ alkyl and
n represents an integer of 1 to 6.

The structure described by the formula (3) is very particularly preferred.

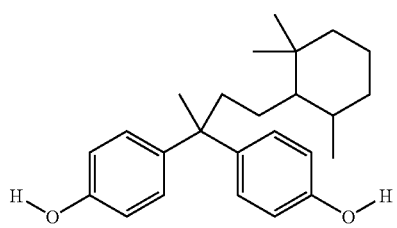

(3)

Surprisingly, it has also been found in this context that the melt viscosity of the polycarbonates obtained based on the novel bisphenol has lower values than the corresponding conventional polycarbonates (at an otherwise comparable molecular weight) both at low and at higher shear rates. This is of importance in particular for the production of injection-molded components, such as e.g. automobile screens. As a result, easier filling of the molds with the usual injection molding machines is possible.

These bisphenols according to the invention may be prepared from phenol derivatives and ketones in an acid-catalysed reaction.

The synthesis of the bisphenols according to the invention is preferably carried out as a condensation reaction of corresponding phenols of the formulas A and B

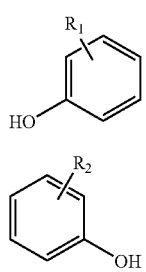

A

B wherein R$^1$ and R$^2$ have the abovementioned meanings, with alkyl-substituted ketones of the formula C

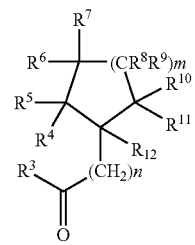

C wherein
R$^3$ to R$^{12}$ have the abovementioned meanings, optionally but not necessarily in the presence of a sulfur-containing compound, preferably with the aid of an acid catalyst, particularly preferably an acid ion exchanger or hydrochloric acid, at temperatures preferably of between 0 and 100° C. with a stoichiometric ratio of phenol derivative to ketone derivative of 15:1 to 2:1.

The phenols of the formulae A and B are known or may be prepared by processes known from the literature, for example by Friedel-Crafts alkylation (Organikum, Organisch-chemisches Grundpraktikum, corrected reprint of the 20th edition, Wiley-VCH, Weinheim, p. 355, 1999). Very many phenols are also commercially obtainable (suppliers e.g. Aldrich, Fluka, Acros etc.).

The ketones of the formula C are also known or may be prepared by processes known from the literature, for example by oxidation of the corresponding alcohols (in this context see also: Cesare Ferri, Reaktionen der organischen Synthese, Technische und präparative Herstellungs- und Umwandlungsverfahren, Georg Thieme Verlag Stuttgart, p. 407 et seq., 1978). Very many ketones are also commercially obtainable (suppliers e.g. Aldrich, Fluka, Acros, Alfa, Avocado etc.).

The very particularly preferred compound 4-(2,2,6-trimethylcyclohexyl)-2-butanone of the formula C may be obtained commercially, for example, from Avocado, from Alfa (a Johnson Matthey company, Karlsruhe, Germany), ChemSampCo, Inc. Trenton, N.J., USA or from Pfaltz & Bauer, Inc. Waterbury, Conn., USA.

The synthesis is described, for example, in L. A. Fowley et al., Tetrahedron Lett., 34(19), 3075, 1993 or in Helv. Chim. Acta, 76(5), 2070, 1993.

The condensation is very particularly preferably carried out with hydrochloric acid as the acid catalyst at temperatures of between 0 and 60° C. with a stoichiometric ratio of phenol derivative (formula A, B) to ketone derivative formula C of 10 to 1, a mercaptan or thiocarboxylic acid compound (e.g. dodecylmercaptan, mercaptopropionic acid or thioacetic acid) preferably being present as the sulfur-containing compound, preferably only in about 0.01 to 25%, based on the ketone compound. The hydrochloric acid is very particularly preferably introduced as HCl gas.

The condensation may be carried out in bulk or in solution. Inert solvents, such as, for example, chlorinated hydrocarbons, such as methylene chloride or dichloroethane, or toluene, xylenes or chlorobenzenes, may be employed here. The reaction is particularly preferably carried out in bulk with an excess of phenol.

The present invention also provides polycarbonates and copolycarbonates prepared using the bisphenols according to the invention, and the corresponding preparation processes. The polycarbonates and copolycarbonates which have been prepared using the bisphenols according to the invention and contain the structural units —O—D—O— derived from the compounds of the formulae 1 to 3 (see also formula 5 below) are represented for example by the general formulae (4a) and (4b)

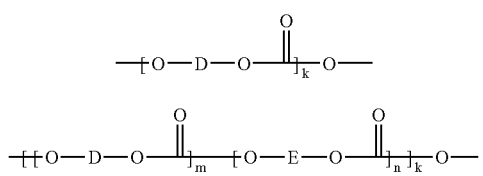

(4a)

(4b)

wherein the radical O—E—O represents any diphenolate radicals, in which —E—, independently of one another, is an aromatic radical having 6 to 40 C atoms which may contain one or more aromatic nuclei or fused aromatic nuclei optionally containing heteroatoms and is optionally substituted by $C_1$–$C_{12}$-alkyl radicals or halogen and may contain aliphatic radicals, cycloaliphatic radicals, aromatic nuclei or heteroatoms as bridge members, and in which k represents an integer between 1 and 1,000, preferably between 1 and 800, particularly preferably between 1 and 600 and very particularly preferably between 1 and 500 and especially preferably between 1 and 300, and m represents a fraction z/k and n represents a fraction (k–z)/k, wherein z represents numbers between 1 and k.

Preferred diphenolate units of the copolycarbonates according to the invention are derived from general structures of the formula (5), $C_{12}$-arylene radical, which may optionally be fused with further aromatic rings containing heteroatoms, and in which o represents an integer between 1 and 1,000, preferably between 1 and 800, particularly preferably between 1 and 600 and very particularly preferably between 1 and 500 and especially preferably between 1 and 300, and p represents a fraction z/o and q represents a fraction (o–z)/o, wherein z represents numbers between 1 and o and n and m are defined as mentioned above for formula (1).

Examples which may be mentioned of the diphenols on which, in addition to the bisphenols according to the invention, the general formulae (4) and (5) are based are hydroquinone, resorcinol, dihydroxybiphenyls, bis-(hydroxyphenyl)-alkanes, bis-(hydroxyphenyl)-cycloalkanes, bis-(hydroxyphenyl) sulfides, bis-(hydroxyphenyl) ethers, bis-(hydroxyphenyl) ketones, bis-(hydroxyphenyl) sulfones, bis-(hydroxyphenyl)-sulfoxides, α,α'-bis-(hydroxyphenyl)-diisopropylbenzenes and nucleus-alkylated and nucleus-halogenated compounds thereof, and also α,ω-bis-(hydroxyphenyl)-polysiloxanes.

Preferred diphenols are, for example, 4,4'-dihydroxybiphenyl (DOD), 4,4'-dihydroxybiphenyl ether (DOD ether), 2,2-bis-(4-hydroxyphenyl)-propane (bisphenol A), 1,1-bis-(4-hydroxyphenyl)-3,3,5-trimethylcyclohexane (bisphenol TMC), 1,1-bis-(4-hydroxyphenyl)-cyclohexane, 2,4-bis-(4-hydroxyphenyl)-2-methylbutane, 1,1-bis-(4-hydroxyphenyl)-1-phenylethane, 1,1-bis-[2-(4-hydroxyphenyl)-2-propyl]-benzene, 1,3-bis-[2-(4-hydroxyphenyl)-2-propyl]-benzene (bisphenol M), 2,2-bis-(3-methyl-4-hydroxyphenyl)-propane, 2,2-bis-(3-chloro-4-hydroxyphenyl)-propane, bis-(3,5-dimethyl-4-hydroxyphenyl)-methane, 2,2-bis-(3,5-dimethyl-4-hydroxyphenyl)-propane, bis-(3,5-dimethyl-4-hydroxyphenyl) sulfone, 2,4-bis-(3,5-dimethyl-4-

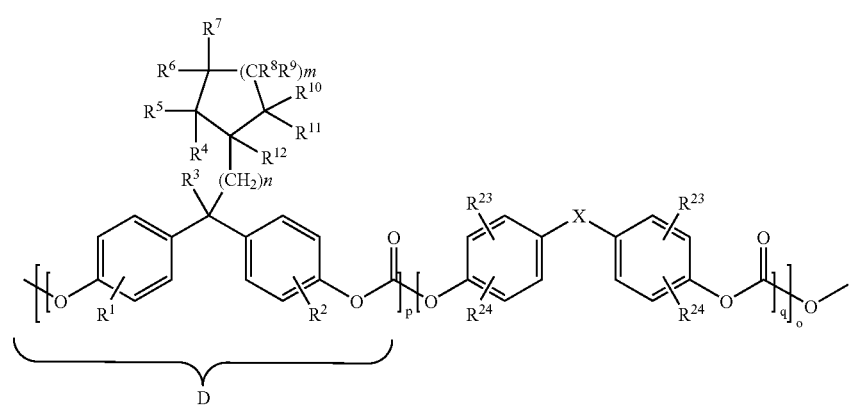

(5)

in which $R^{23}$ and $R^{24}$ independently of one another represent H, linear or branched $C_1$–$C_{18}$ alkyl or alkoxy radicals, halogen, such as Cl or Br, or an optionally substituted aryl or aralkyl radical, preferably H or linear or branched $C_1$–$C_{12}$ alkyl, particularly preferably H or $C_1$–$C_8$ alkyl radicals and very particularly preferably H or methyl, $R^3$ and $R^4$ represent linear or branched $C_1$–$C_{10}$-alkyl and X represents a single bond, —$SO_2$—, —CO—, —O—, —S—, a $C_1$- to $C_6$-alkylene, $C_2$- to $C_5$-alkylidene or $C_5$- to $C_6$-cycloalkylidene radical, which may be substituted by $C_1$- to $C_6$-alkyl, preferably methyl or ethyl radicals, or a $C_6$- to hydroxyphenyl)-2-methylbutane, 2,2-bis-(3,5-dichloro-4-hydroxyphenyl)-propane and 2,2-bis-(3,5-dibromo-4-hydroxyphenyl)-propane.

Particularly preferred diphenols are, for example, 2,2-bis-(4-hydroxyphenyl)-propane (bisphenol A), 4,4'-dihydroxybiphenyl (DOD), 4,4'-dihydroxybiphenyl ether (DOD ether), 1,3-bis-[2-(4-hydroxyphenyl)-2-propyl]-benzene (bisphenol M), 2,2-bis-(3,5-dimethyl-4-hydroxyphenyl)-propane, 1,1-bis-(4-hydroxyphenyl)-1-phenylethane, 2,2-bis-(3,5-dichloro-4-hydroxyphenyl)-propane, 2,2-bis-(3,5-dibromo-4-hydroxyphenyl)-propane, 1,1-bis-(4- hydroxyphenyl)-cyclohexane and 1,1-bis-(4-hydroxyphenyl)-3,3,5-trimethylcyclohexane (bisphenol TMC). 2,2-Bis-(4-hydroxyphenyl)-propane (bisphenol A), 4,4'-dihydroxybiphenyl (DOD), 1,3-bis-[2-(4-hydroxyphenyl)-2-propyl]-benzene (bisphenol M) and 1,1-bis-(4-hydroxyphenyl)-3,3,5-trimethylcyclohexane (bisphenol TMC) are very particularly preferred.

The diphenols may be used both by themselves and in a mixture with one another; both homopolycarbonates and copolycarbonates are included. The diphenols are known from the literature or may be prepared by processes known from the literature (see e.g. H. J. Buysch et al., Ullmann's Encyclopedia of Industrial Chemistry, VCH, New York 1991, 5th ed., vol. 19, p. 348). The polycarbonates and copolycarbonates may also be branched. Certain small amounts, preferably amounts of between 0.05 and 5 mol %, particularly preferably 0.1 to 3 mol %, very particularly preferably 0.1 to 2 mol %, based on the moles of diphenols employed, of trifunctional or tetrafunctional compounds, such as e.g. isatin-biscresol (IBC) or phloroglucinol, 4,6-dimethyl-2,4,6-tri-(hydroxyphenyl)-hept-2-ene; 4,6-dimethyl-2,4,6-tri-(4-hydroxyphenyl)-heptane; 1,3,5-tri-(4-hydroxyphenyl)-benzene; 1,1,1-tri-(4-hydroxyphenyl)-ethane (THPE); tri-(4-hydroxyphenyl)-phenylmethane; 2,2-bis-[4, 4-bis-(4-hydroxyphenyl)-cyclohexyl]-propane; 2,4-bis-(4-hydroxyphenyl-isopropyl)-phenol; 2,6-bis-(2-hydroxy-5'-methyl-benzyl)-4-methylphenol; 2-(4-hydroxyphenyl)-2-(2, 4-dihydroxyphenyl)-propane; hexa-(4-(4-hydroxyphenyl-isopropyl)-phenyl)-orthoterephthalic acid ester; tetra-(4-hydroxyphenyl)-methane; tetra-(4-(4-hydroxyphenyl-isopropyl)-phenoxy)-methane; -tris-(4-hydroxyphenyl)-1,3, 5-triisopropylbenzene; 2,4-dihydroxybenzoic acid; trimesic acid; cyanuric chloride; 3,3-bis-(3-methyl-4-hydroxyphenyl)-2-oxo-2,3-dihydroindole; 1,4-bis-(4',4"-dihydroxytriphenyl)-methyl)-benzene and in particular: 1,1,1-tri-(4-hydroxyphenyl)-ethane and bis-(3-methyl-4-hydroxyphenyl)-2-oxo-2,3-dihydroindole are employed for this purpose. Isatin-biscresol and 1,1,1-tri-(4-hydroxyphenyl)-ethane and bis-(3-methyl-4-hydroxyphenyl)-2-oxo-2,3-dihydroindole may preferably be employed as branching agents.

Branched structures result by the use of these branching agents. The resulting long-chain branching leads to rheological properties of the polycarbonates obtained, which manifests itself in a structural viscosity (non-Newtonian flow behavior) compared with linear types.

The present invention furthermore relates to a process for the preparation of the polycarbonates and copolycarbonates that contain structural units conforming to any of the formulae (4a), (4b) and (5) according to the invention, characterized in that bisphenols and optionally branching agents are dissolved in an aqueous alkaline solution and are reacted with a source of carbonate, such as phosgene, optionally dissolved in a solvent, in a two-phase mixture of an aqueous alkaline solution, an organic solvent and a catalyst, preferably an amine compound. The reaction may also be carried out in several stages. Such processes for the preparation of polycarbonate are known as two-phase boundary processes e.g. from H. Schnell, Chemistry and Physics of Polycarbonates, Polymer Reviews, vol. 9, Interscience Publishers, New York 1964, p. 33 et seq. and from Polymer Reviews, vol. 10, "Condensation Polymers by Interfacial and Solution Methods", Paul W. Morgan, Interscience Publishers, New York 1965, chap. VIII, p. 325, and the fundamental conditions are therefore familiar to the expert.

The concentration of the bisphenols in the aqueous alkaline solution is 2 to 25 wt. %, preferably 2 to 20 wt. %, particularly preferably 2 to 18 wt % and very particularly preferably 3 to 15 wt. %. The aqueous alkaline solution comprises water, in which hydroxides of alkali metals or alkaline earth metals are dissolved. Sodium hydroxide and potassium hydroxide are preferred.

If phosgene is used as the source of carbonate, the volume ratio of aqueous alkaline solution to organic solvent is 5:95 to 95:5, preferably 20:80 to 80:20, particularly preferably 30:70 to 70:30 and very particularly preferably 40:60 to 60:40. The molar ratio of bisphenol to phosgene is less than 1:10, preferably less than 1:6, particularly preferably less than 1:4 and very particularly preferably less than 1:3. The concentration of the branched polycarbonates and copolycarbonates according to the invention in the organic phase is 1.0 to 25 wt. %, preferably 2 to 20 wt. %, particularly preferably 2 to 18 wt. % and very particularly preferably 3 to 15 wt %.

The concentration of the amine compound, based on the amount of bisphenol employed, is 0.1 to 10 mol %, preferably 0.2 to 8 mol %, particularly preferably 0.3 to 6 mol % and very particularly preferably 0.4 to 5 mol %.

The source of carbonate is phosgene, diphosgene or triphosgene, preferably phosgene. In the case where phosgene is employed, a solvent may optionally be dispensed with and the phosgene may be introduced directly into the reaction mixture.

Catalysts which may be employed are tertiary amines, such as triethylamine or N-alkylpiperidines. Suitable catalysts are trialkylamines and 4-(dimethylamino)pyridine. Triethylamine, tripropylamine, triisopropylamine, tributylamine, triisobutylamine, N-methylpiperidine, N-ethylpiperidine and N-propylpiperidine are particularly suitable.

Suitable organic solvents are halogenated hydrocarbons, such as methylene chloride and/or chlorobenzene, dichlorobenzene, trichlorobenzene or mixtures thereof, or aromatic hydrocarbons, such as, e.g. toluene or xylenes.

The reaction temperature may be −5° C. to 100° C., preferably 0° C. to 80° C., particularly preferably 10° C. to 70° C. and very particularly preferably 10° C. to 60° C.

Alternatively, the polycarbonates according to the invention may also be prepared by the melt transesterification process. The melt transesterification process is described, for example, in the Encyclopedia of Polymer Science, vol. 10 (1969), Chemistry and Physics of Polycarbonates, Polymer Reviews, H. Schnell, vol. 9, John Wiley and Sons, Inc. (1964) and DE-C 10 31 512.

In the melt transesterification process, the aromatic dihydroxy compounds already 5 described above in connection with the phase boundary process are transesterified with carbonic acid diesters with the aid of suitable catalysts and optionally further additives in the melt.

Carbonic acid diesters in the context of the invention are those of the formula (6) and (7)

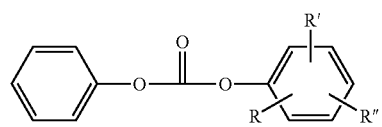

6

-continued

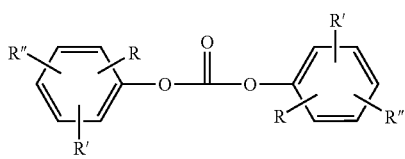

7 wherein

R, R' and R" independently of one another may represent H, optionally branched $C_1$–$C_{34}$-alkyl/cycloalkyl, $C_7$–$C_{34}$-alkaryl or $C_6$–$C_{34}$-aryl, for example diphenyl carbonate, butylphenyl phenyl carbonate, di-butylphenyl carbonate, isobutylphenyl phenyl carbonate, di-isobutylphenyl carbonate, tert-butylphenyl phenyl carbonate, di-tert-butylphenyl carbonate, n-pentylphenyl phenyl carbonate, di-(n-pentylphenyl) carbonate, n-hexylphenyl phenyl carbonate, di-(n-hexylphenyl) carbonate, cyclohexylphenyl phenyl carbonate, di-cyclohexylphenyl carbonate, phenylphenol phenyl carbonate, di-phenylphenol carbonate, isooctylphenyl phenyl carbonate, di-isooctylphenyl carbonate, n-nonylphenyl phenyl carbonate, di-(n-nonylphenyl) carbonate, cumylphenyl phenyl carbonate, di-cumylphenyl carbonate, naphthylphenyl phenyl carbonate, di-naphthylphenyl carbonate, di-tert-butylphenyl phenyl carbonate, di-(di-tert-butylphenyl) carbonate, dicumyphenyl phenyl carbonate, di-(dicumylphenyl) carbonate, 4-phenoxyphenyl phenyl carbonate, di-(4-phenoxyphenyl) carbonate, 3-pentadecylphenyl phenyl carbonate, di-(3-pentadecylphenyl) carbonate tritylphenyl phenyl carbonate and di-tritylphenyl carbonate, preferably diphenyl carbonate, tert-butylphenyl phenyl carbonate, di-tert-butylphenyl carbonate, phenylphenol phenyl carbonate, di-phenylphenol carbonate, cumylphenyl phenyl carbonate and di-cumylphenyl carbonate, particularly preferably diphenyl carbonate.

Mixtures of the carbonic acid diesters mentioned may also be employed.

The content of carbonic acid ester is 100 to 130 mol %, preferably 103 to 120 mol %, particularly preferably 103 to 109 mol %, based on the dihydroxy compound.

Basic catalysts are known and include, for example, alkali metal and alkaline earth metal hydroxides and oxides, and also ammonium or phosphonium salts, called onium salts in the following, are employed in the melt transesterification process as catalysts in the context of the invention. Onium salts are preferably employed here, particularly preferably phosphonium salts. Phosphonium salts in the context of the invention are those of the formula (8)

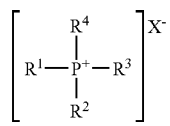

8 wherein $R^{1-4}$ independently one of the other are $C_1$–$C_{10}$-alkyls, $C_6$–$C_{10}$-aryls, $C_7$–$C_{10}$-aralkyls or $C_5$–$C_6$-cycloalkyls, preferably methyl or $C_6$–$C_{14}$-aryls, particularly preferably methyl or phenyl, and $X^-$ denotes an anion, such as hydroxide, sulfate, hydrogen sulfate, bicarbonate, carbonate, a halide, preferably chloride, or an alcoholate of the formula OR, wherein R may be $C_6$–$C_{14}$-aryl or $C_7$–$C_{12}$-aralkyl, preferably phenyl.

Preferred catalysts are tetraphenylphosphonium chloride, tetraphenylphosphonium hydroxide and tetraphenylphosphonium phenolate, particularly preferably tetraphenylphosphonium phenolate.

The catalysts are preferably employed in amounts of $10^{-8}$ to $10^{-3}$ mol, based on one mole of bisphenol, particularly preferably in amounts of $10^{-7}$ to $10^{-4}$ mol.

Further catalysts may be used by themselves or optionally in addition to the onium salt in order to increase the speed of the polymerization. These include salts of alkali metals and alkaline earth metals, such as hydroxides, alkoxides and aryloxides of lithium, sodium and potassium, preferably hydroxide, alkoxide or aryloxide salts of sodium. Sodium hydroxide and sodium phenolate are most preferred. The amounts of the cocatalyst may be in the range from 1 to 200 ppb, preferably 5 to 150 ppb and most preferably 10 to 125 ppb, in each case calculated as sodium.

The transesterification reaction of the aromatic dihydroxy compound and the carbonic acid diester in the melt is preferably carried out in two stages. In the first stage melting of the aromatic dihydroxy compound and the carbonic acid diester takes place at temperatures of 80 to 250° C., preferably 100 to 230° C., particularly preferably 120 to 190° C. under normal pressure in the course of 0 to 5 hours, preferably 0.25 to 3 hours. After addition of the catalyst, the oligocarbonate is prepared from the aromatic dihydroxy compound and the carbonic acid diester by distilling off the monophenol by applying a vacuum (down to 2 mm Hg) and increasing the temperature (up to 260° C.). The main amount of vapors are obtained from the process by this means. The oligocarbonate prepared in this way has a weight-average molecular weight $M_w$ (determined by measurement of the rel. solution viscosity in methylene chloride or in mixtures of the same amounts by weight of phenol/o-dichlorobenzene calibrated by light scattering) in the range from 2,000 g/mol to 18,000 g/mol, preferably 4,000 g/mol to 15,000 g/mol.

In the second stage the polycarbonate is prepared in the polycondensation by further increasing the temperature to 250 to 320° C., preferably 270 to 295° C., under a pressure of <2 mm Hg. The remainder of the vapors are removed from the process by this means.

The catalysts may also be employed in combination (two or more) with one another.

If alkali metal/alkaline earth metal catalysts are employed, it may be advantageous to add the alkali metal/alkaline earth metal catalysts at a later point in time (e.g. after the oligocarbonate synthesis, in the polycondensation in the second stage).

The reaction of the aromatic dihydroxy compound and the carbonic acid diester to yield the polycarbonate may be carried out discontinuously or, preferably, continuously in the context of the process according to the invention, for example in stirred tanks, thin film evaporators, falling film evaporators, cascades of stirred tanks, extruders, kneaders, simple disc reactors and high-viscosity disc reactors.

Analogously to the phase boundary process, branched poly- or copolycarbonates may be prepared by using polyfunctional compounds.

The weight average molecular weights (Mw) of the branched polycarbonates and copolycarbonates according to the invention are in the range from 6,000 to 200,000 g/mol, preferably between 6,000 and 100,000 g/mol, particularly preferably between 10,000 and 80,000 g/mol and very particularly preferably between 12,000 and 70,000 g/mol (determined by means of GPC and polycarbonate calibration).

Preferred, particularly preferred or very particularly preferred embodiments are those which use the parameters, compounds, definitions and explanations given under preferred, particularly preferred or very particularly preferred or preferably etc.

However, the definitions, parameters, compounds and explanations mentioned generally in the description or mentioned in preferred ranges may also be combined with one another as desired, that is to say between the particular ranges and preferred ranges.

The polycarbonates and copolycarbonates according to the invention may be worked up in a known manner and processed to any desired shaped articles, for example by extrusion, injection molding or extrusion blow molding.

Other aromatic polycarbonates and/or other aromatic polyester-carbonates and/or other aromatic polyesters may also be admixed with the polycarbonates and copolycarbonates according to the invention in a known manner, for example by compounding.

The conventional additives for these thermoplastics, such as fillers, UV stabilizers, heat stabilizers, antistatics and pigments, may also be added to the polycarbonates and copolycarbonates according to the invention in the conventional amounts; if appropriate, the mold release properties, the flow properties and/or the flame resistance may also be improved by addition of external mold release agents, flow agents and/or flameproofing agents (e.g. alkyl and aryl phosphites, phosphates, -phosphanes and low molecular weight carboxylic acid esters, halogen compounds, salts, chalk, quartz flour, glass fibers and carbon fibers, pigments and a combination thereof. Such compounds are described e.g. in WO 99/55772, p. 15–25, and in the corresponding chapters of the "Plastics Additives Handbook", ed. Hans Zweifel, 5th edition 2000, Hanser Publishers, Munich).

The polycarbonates and copolycarbonates according to the invention, optionally in a blend with other thermoplastics and/or conventional additives, when processed to any desired shaped articles/extrudates, may be employed in all instances where polycarbonates, polyester-carbonates and polyesters which are already known are employed. On the basis of their profile of properties, they are suitable in particular as materials for injection molding of relatively large moldings, for example automobile screens. Due to the low water uptake and the associated improved dimensional stability, however, they are also particularly suitable as substrate materials for optical data storage media, such as e.g. CDs, CD-Rs, DVDs, DVD-Rs, blue-ray discs or advanced optical discs (AOD), but may also be employed, for example, as films in the electrical sector, as moldings in vehicle construction and as sheets for covers in the safety sector. Further possible uses of the polycarbonates according to the invention are:

1. Safety panes, which as is known are necessary in many areas of buildings, vehicles and aircraft, and as helmet shields.
2. Production of foils, in particular ski foils.
3. Production of blow moldings (see, for example, U.S. Pat. No. 2,964,794), for example 1 to 5 gallon water bottles.
4. Production of transparent sheets, in particular hollow sheets, for example for covering buildings such as railway stations, greenhouses and lighting installations.
5. Production of optical data storage media.
6. For the production of traffic light housings or traffic signs.
7. For the production of foams (see, for example, DE-B 1 031 507).
8. For the production of filaments and wires (see, for example, DE-B 1 137 167 and DE-A 1 785 137).
9. As translucent plastics with a content of glass fibers for illumination purposes (see, for example, DE-A 1 554 020).
10. As translucent plastics with a content of barium sulfate, titanium dioxide and/or zirconium oxide or organic polymeric acrylate rubbers (EP-A 634 445, EP-A 269324) for the production of transparent and light-scattering moldings.
11. For the production of precision injection molding components, such as, for example, lens holders. Polycarbonates with a content of glass fibers, which optionally additionally comprise about 1 to 10 wt. % $MoS_2$, based on the total weight, are used for this.
12. For the production of optical equipment components, in particular lenses for photographic and film cameras (see, for example, DE-A 2 701 173).
13. As light transmission carriers, in particular as light conductor cables (see, for example, EP-A 0 089 801).
14. As electrical insulating materials for electrical conductors and for plug housings and plug connectors.
15. Production of mobile telephone housings with improved resistance to perfume, shaving lotion and skin perspiration.
16. Network interface devices.
17. As a carrier material for organic photoconductors.
18. For the production of lamps, e.g. searchlight lamps, as so-called "head-lamps", diffusing screens or internal lenses, as well as long-distance lamps.
19. For medical uses, e.g. oxygenators, dialysers.
20. For foodstuffs uses, such as e.g. bottles, utensils and chocolate molds.
21. For uses in the automobile sector where contact with fuels and lubricants may occur, such as, for example, bumpers, optionally in the form of suitable blends with ABS or suitable rubbers.
22. For sports articles, such as e.g. slalom poles or ski boot buckles.
23. For household articles, such as e.g. kitchen sinks and letterbox housings.
24. For housings, e.g. electrical distribution cabinets.
25. Housings for electric toothbrushes and hairdryer housings.
26. Transparent washing machine portholes with improved resistance to the wash solution.
27. Safety glasses, visors or optical corrective glasses.
28. Lamp covers for kitchen equipment with improved resistance to kitchen vapor, in particular oil vapors.
29. Packaging films for medicaments.
30. Chip boxes and chip carriers.
31. For other uses, such as e.g. fattening stall doors or animal cages.
32. Safety helmets.

The novel (co)polycarbonate of the present invention are suitable for the preparation of molded and extruded articles.

The following examples are intended to illustrate the invention, but without limiting it.

EXAMPLES

Example 1

Synthesis of a bisphenol based on hydrogenated β-ionone:

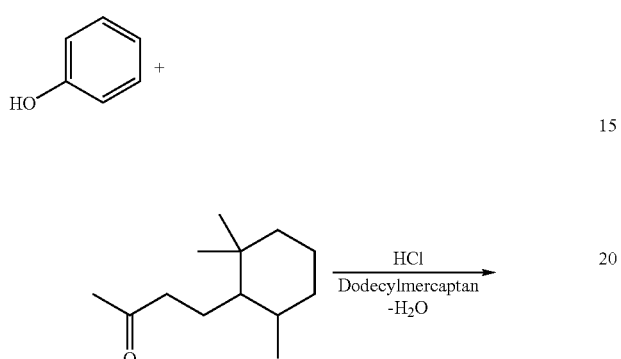

105.9 g (1.13 mol) of freshly distilled phenol and 75 g (0.38 mol) 4-(2,2,6-trimethylcyclohexyl)-2-butanone (Avocado) are initially introduced into the reaction vessel, and 7.5 g (0.037 mol) dodecylmercaptan (Acros) are added as a catalyst. HCl gas is introduced at a constant temperature of 26 to 28° C. for 2 hours. For a condensation which is as complete as possible, the mixture is then subsequently stirred for a further 4 hours at room temperature without further introduction of HCl gas. The reaction mixture was then left to stand overnight at room temperature. To remove the HCl residues, dry nitrogen was passed through the solution at a temperature of 32 to 40° C. for 5 hours. For working up of the reaction mixture, the excess phenol was distilled off first under a water pump vacuum and finally at a max. temperature of 150° C. under an oil pump vacuum with a rotary disc pump. The crude product was finally taken up in methylene chloride and the mixture was washed neutral with water. After concentration of the organic phase and drying of the residue, 122 g of product, which was still contaminated, were obtained. For further purification, the crude product was taken up in 150 ml petroleum ether and the mixture was boiled for 2 hours. During this operation the crude product became increasingly lighter in color. After decanting, the product was boiled up again a total of 2 times with 150 ml n-hexane for 30 min. After decanting, a beige product is obtained, and was dried at 50° C. in a vacuum drying cabinet.

Yield: 71.9 g (0.196 mol, 51.7% of theory)

Analysis:

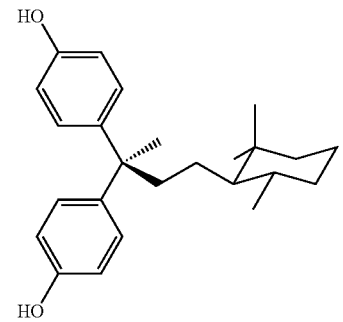

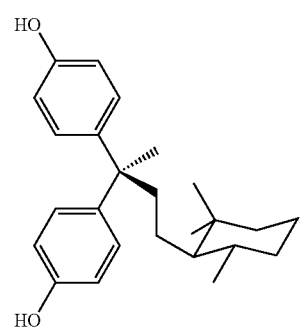

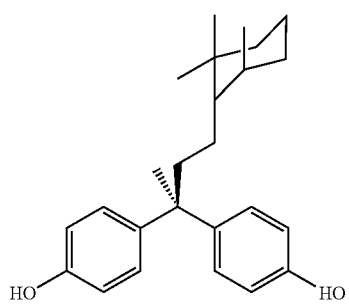

GC-MS gives a double signal lying very closely side by side (stereoisomers) each with the mass 366 (TMS-MW=510).

$^1$H-NMR (400 MHz, TMS, DMSO) δ=9.05 (s, 2O $\underline{H}$), 6.95 (d, AA', 2H$_{ar}$), 6.65 (d, BB', 2H$_{ar}$), 2.0–1.78 (mm, 3H), 1.49 (s, 3H), 1.39–1.27 (m, 2H), 1.27–1.15 (m, 1H), 1.14–1.10 (m, 1H), 1.10–0.81 (m, 5H), 0.87 (s, 3H), 0.72 (s, 3H), 0.69–0.67 (d, 3H).

Example 2 a) Synthesis of the homopolycarbonate:

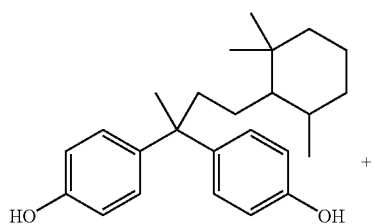

+

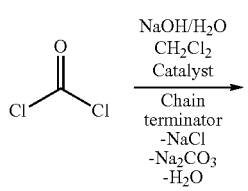

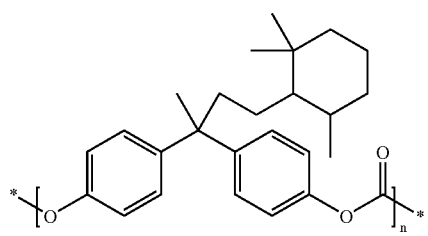

267 ml methylene chloride are added to a solution, which has been rendered inert with nitrogen, of 36.65 g (0.1 mol) bisphenol from example 1 and 8.8 g (0.22 mol) sodium hydroxide in 550 ml water. 0.45 g (0.003 mol or 3.0 mol % with respect to the bisphenol) p-tert-butylphenol (BUP) is added in a one-stage procedure as a chain terminator. 14 ml (20.3 g, 0.205 mol) phosgene are added at a pH of 14 and a temperature of 16° C. in the course of 10 minutes. In order not to allow the pH to fall below 12, 25% strength sodium hydroxide solution was added during the phosgenation. After the phosgenation and flushing with nitrogen has ended, 0.11 g (0.001 mol, 1 mol % with respect to the bisphenol) n-ethylpiperidine is added as a catalyst and the mixture is subsequently stirred for 1 hour. After the aqueous phase has been separated off, the organic phase is acidified with phosphoric acid and washed neutral and salt-free with distilled water. After the polymer has been precipitated out in methanol, 34.2 g polycarbonate are obtained.

Analysis:
Relative solution viscosity in methylene chloride (0.5 g/100 ml solution): 1.163/1.164
GPC (calibration against BPA polycarbonate): molecular weight Mw=25,979, Mn=8,750, polydispersity D=2.97
Glass transition temperature $T_g$: 145° C.

b) A homopolycarbonate with a higher molecular weight is prepared in an analogous manner (only a lower chain terminator concentration). A product with the following analytical data is obtained by this procedure:

Analysis:
Relative solution viscosity in methylene chloride (0.5 g/100 ml solution): 1.230/1.230
GPC (calibration against BPA polycarbonate): molecular weight Mw=31,424, Mn=13,779, polydispersity D=2.28
Glass transition temperature $T_g$: 149° C.

Example 3

Determination of the viscosity as a function of the shear rate (ISO 11443).

The polycarbonate obtained in example 2 is analysed Theologically at 290° C. The following data are obtained in this analysis:

| Shear gradient [s$^{-1}$] | Viscosity [Pas] |
|---|---|
| 50 | 365 |
| 100 | 323 |
| 200 | 276 |
| 500 | 212 |
| 1,000 | 166 |
| 1,500 | 140 |

Example 4

Comparison Example

For comparison, a linear BPA polycarbonate (Makrolon 2608, Bayer AG) with a molecular weight Mw=26,000 is used analogously to example 3.

| Shear gradient [s$^{-1}$] | Viscosity [Pas] |
|---|---|
| 50 | 688 |
| 100 | 625 |
| 200 | 563 |
| 500 | 480 |
| 1,000 | 383 |
| 1,500 | 318 |

As may be seen from the comparison of the viscosity data between example 3 and 4, at approximately the same molecular weight the melt viscosity at 290° C. is lower over the entire range of the shear gradient. The polycarbonate according to the invention from example 2 thus flows more readily than the comparison material based on bisphenol A (Makrolon 2608).

Example 5

Synthesis of copolycarbonates with bisphenol A with different compositions (50:50), (75:25), (25:75):

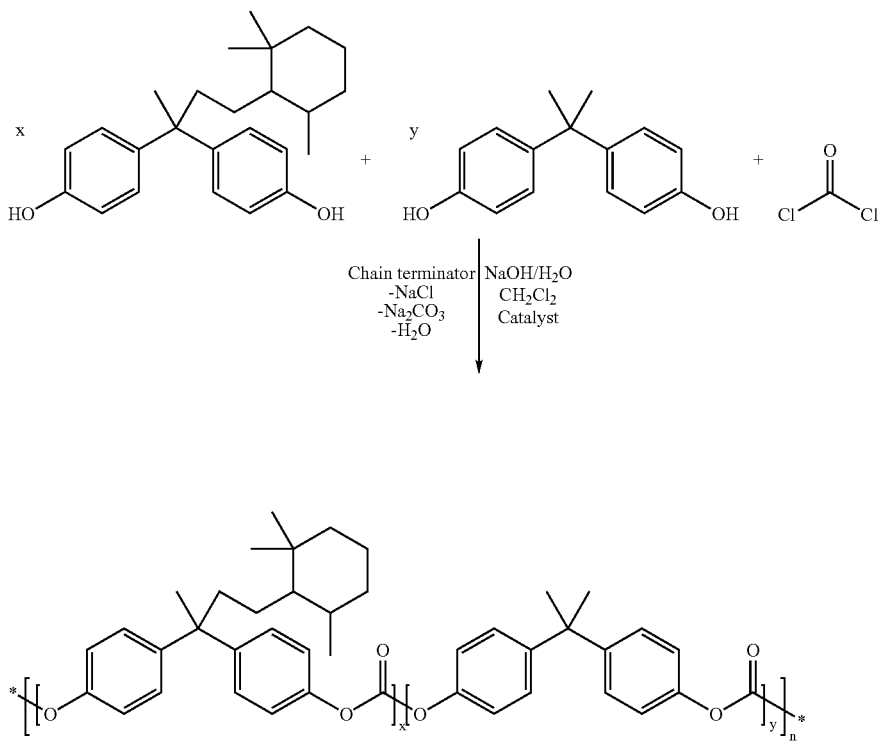

a) 220 ml methylene chloride are added to a solution, which has been rendered inert with nitrogen, of 18.33 g (0.05 mol) bisphenol from example 1, 11.42 g (0.05 mol) bisphenol A and 8.8 g (0.22 mol) sodium hydroxide in 520 ml water. 0.45 g (0.003 mol or 3.0 mol % with respect to the bisphenol) p-tert-butylphenol (BUP) is added in a one-stage procedure as a chain terminator. 14 ml (20.6 g, 0.208 mol) phosgene are added at a pH of 14 and a temperature of 16° C. in the course of 10 minutes. In order not to allow the pH to fall below 12, 25% strength sodium hydroxide solution was added during the phosgenation. After the phosgenation and flushing with nitrogen has ended, 0.11 g (0.001 mol, 1 mol % with respect to the bisphenol) n-ethylpiperidine is added as a catalyst and the mixture is subsequently stirred for 1 hour. After the aqueous phase has been separated off, the organic phase is acidified with phosphoric acid and washed neutral and salt-free with distilled water. After the polymer has been precipitated out in methanol, 20.1 g polycarbonate are obtained.

Analysis 5a):
Relative solution viscosity in methylene chloride (0.5 g/100 ml solution): 1.161/1.161

GPC (calibration against BPA polycarbonate): molecular weight Mw=20,414, Mn=5,926, polydispersity D=3.44

Glass transition temperature $T_g$: 140° C.

The following copolycarbonates which differ in their composition (bisphenol A to bisphenol from example 1) are prepared analogously to this procedure.

| Copolycarbonate | Bisphenol A [mol %] | Bisphenol from example 1 [mol %] |
|---|---|---|
| 5b) | 75 | 25 |
| 5c) | 25 | 75 |

The following polymers are obtained by this procedure:

| Copolycarbonate | Eta rel | Mw | Mn | D | Tg[° C.] |
|---|---|---|---|---|---|
| 5b) | 1.336 | 38,737 | 16,377 | 2.37 | 150 |
| 5c) | 1.233 | 30,321 | 8,615 | 3.52 | 148 |

Example 6

Synthesis of asymmetrically and symmetrically substituted bisphenols:

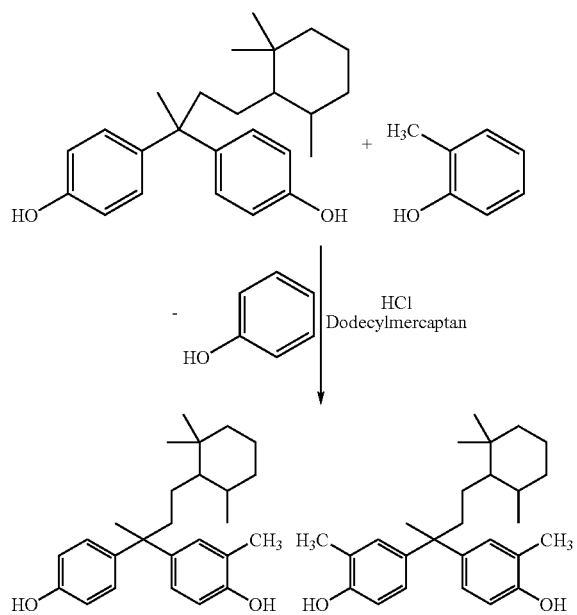

17.59 g (0.048 mol) bisphenol from example 1 and 153.8 g (1.42 mol) o-cresol are initially introduced into the reaction vessel, and 0.97 g (0.0048 mol) dodecylmeraptan is added as a catalyst. The mixture is homogenized at 40° C. HCl gas is then introduced to the reaction mixture at 40° C. for four hours. The mixture is subsequently stirred at this temperature for a further 1.5 hours without further introduction of gas. The reaction mixture then remained overnight at room temperature. To remove the HCl residues, dry nitrogen was passed through the solution at room temperature for 1 hour. For working up of the reaction mixture, the excess cresol was distilled off first under a water pump vacuum and finally at a max. temperature of 150° C. under an oil pump vacuum with a rotary disc pump. 18.6 g of product is obtained.

Analysis:
GC-MS gives a triple signal lying very closely side by side (product mixture) with in each case the educt mass 366 (TMS-MW=510), the product mass 380 (TMS-MW=524) for the monosubstituted product and the product mass 394 (TMS-MW=538) for the disubstituted product.

The ratio of the GC-MS mass signals of the various (silylated) components is 0.600 (educt): 1.295 (monosubst. product): 1.0 (disubst. product).

$^1$H-NMR (400 MHz, TMS, DMSO): The previous AA'BB' splitting pattern for para-substituted aromatics in the aromatic resonance range at δ=6.95 (d, AA', 2H$_{ar}$), 6.65 (d, BB', 2H$_{ar}$) (see example 1) changes into the typical splitting pattern for polysubstituted aromatics. Furthermore, in addition to δ=9.00 (s, O$\underline{H}$), a further signal occurs for a phenolic OH group at δ=9.12 (s, O$\underline{H}$). The expected signal for the methyl groups on the aromatic ring occurs at δ=2.05 (s, C$\underline{H}_3$).

Example 7

70.36 g (0.192 mol) bisphenol prepared analogously to example 1 and 615.2 g (5.68 mol) o-cresol are initially introduced into the reaction vessel, and 3.88 g (0.0192 mol) dodecylmercaptan are added as a catalyst. The mixture is homogenized at 50° C. HCl gas is then introduced to the reaction mixture at 50° C., and the temperature is lowered to 40° C. immediately after a clear change in color occurs. The introduction of the gas is maintained for 7 hours at this temperature. To remove the HCl residues, dry nitrogen was passed through the solution at room temperature for 1 hour. For working up of the reaction mixture, the excess cresol was distilled off first under a water pump vacuum and finally at a max. temperature of 150° C. under an oil pump vacuum with a rotary disc pump. 59.45 g of product are obtained.

Analysis:
GC-MS gives a signal for the disubstituted product with the mass 394 (TMS-MW=538)

The ratio of the GC-MS mass signals (area %) of the various (silylated) components is 0.38 (monosubst. product): 94.58 (disubst. product).

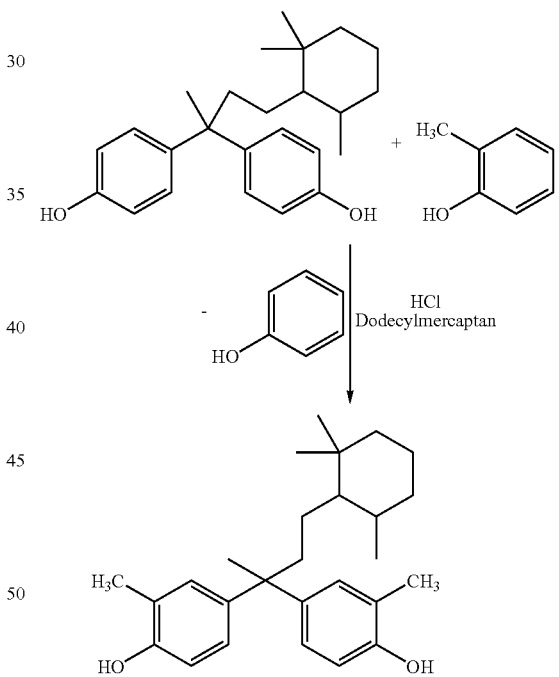

Example 8

Synthesis of a bisphenol based on hydrogenated β-ionone with an ion exchanger:

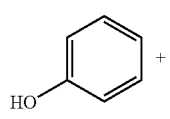

-continued

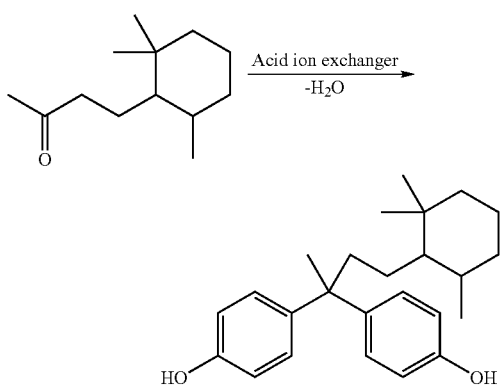

110.25 g (1.17 mol) of freshly distilled phenol and 23 g (0.117 mol) 4-(2,2,6-trimethylcyclohexyl)-2-butanone (Avocado) are initially introduced into the reaction vessel, and 100 g of dried, active ion exchanger K1221 (Bayer AG, Leverkusen) are added as a catalyst. The mixture is stirred at a constant temperature of 70° C. for 24 hours. Thereafter, the complete mixture is introduced on to a suction filter with polyacrylonitrile fabric and the catalyst is separated off. Rinsing was carried out with fresh phenol. The filtrate was freed from excess phenol first under a water pump vacuum and then under an oil pump vacuum at 90° C. After purification with petroleum ether analogously to example 1, the desired product is obtained in a yield of 20 g.

Analysis:
$^1$H-NMR (400 MHz, TMS, DMSO) data as under example 1.

Example 9 a) Synthesis of a copolycarbonate with bisphenol TMC (50:50):

220 ml methylene chloride are added to a solution, which has been rendered inert with nitrogen, of 18.33 g (0.05 mol) bisphenol from example 1, 15.52 g (0.05 mol) bisphenol TMC and 8.8 g (0.22 mol) sodium hydroxide in 420 ml water. 0.45 g (0.003 mol or 3.0 mol % with respect to the bisphenol) p-tert-butylphenol (BUP) is added in a one-stage procedure as a chain terminator. 14 ml (20.6 g, 0.208 mol) phosgene are added at a pH of 14 and a temperature of 16° C. in the course of 10 minutes. In order not to allow the pH to fall below 12, 25% strength sodium hydroxide solution was added during the phosgenation. After the phosgenation and flushing with nitrogen has ended, 0.11 g (0.001 mol, 1 mol % with respect to the bisphenol) n-ethylpiperidine is added as a catalyst and the mixture is subsequently stirred for 1 hour. After the aqueous phase has been separated off, the organic phase is acidified with phosphoric acid and washed neutral and salt-free with distilled water. After the polymer has been precipitated out in methanol, 30.5 g polycarbonate are obtained.

Analysis:
Relative solution viscosity in methylene chloride (0.5 g/100 ml solution): 1.147/1.148
GPC (calibration against BPA polycarbonate): molecular weight Mw=16,986, Mn=6,150, polydispersity D=2.76
Glass transition temperature $T_g$: 181° C.

b) Synthesis of a copolycarbonate with bisphenol TMC (30:70): 220 ml methylene chloride are added to a solution, which has been rendered inert with nitrogen, of 25.66 g (0.07 mol) bisphenol from example 1 (70 mol %), 9.31 g (0.03 mol) bisphenol TMC (30 mol %) and 8.8 g (0.22 mol) sodium hydroxide in 600 ml water. 0.45 g (0.003 mol or 3.0 mol % with respect to the bisphenol) p-tert-butylphenol (BUP) is added in a one-stage procedure as a chain terminator. 14 ml (20.6 g, 0.208 mol) phosgene are added at a pH of 14 and a temperature of 16° C. in the course of 10 minutes. In

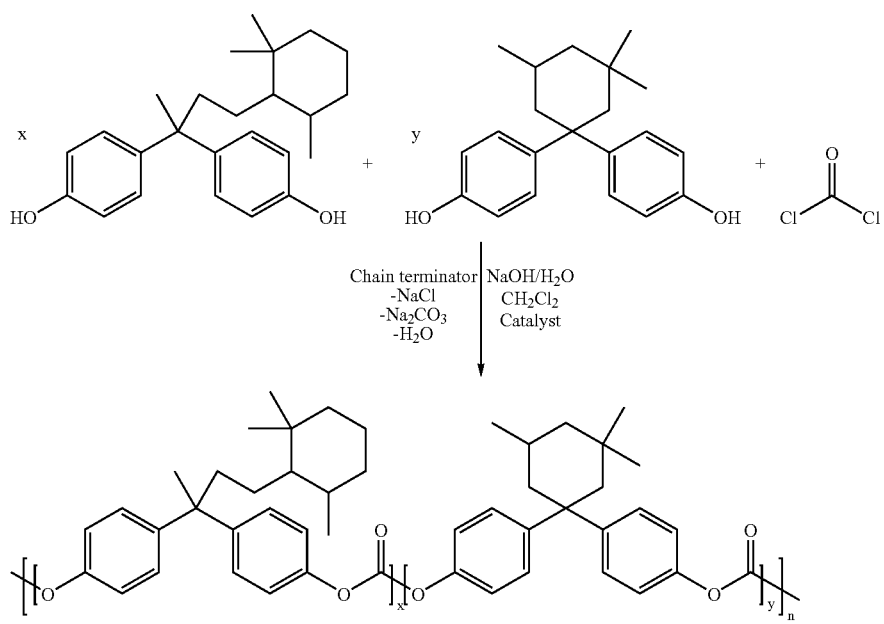

order not to allow the pH to fall below 12, 25% strength sodium hydroxide solution was added during the phosgenation. After the phosgenation and flushing with nitrogen has ended, 0.11 g (0.001 mol, 1 mol % with respect to the bisphenol) n-ethylpiperidine is added as a catalyst and the mixture is subsequently stirred for 1 hour. After the aqueous phase has been separated off, the organic phase is acidified with phosphoric acid and washed neutral and salt-free with distilled water. After the polymer has been precipitated out in methanol, 34.1 g polycarbonate are obtained.

Analysis:
Relative solution viscosity in methylene chloride (0.5 g/100 ml solution): 1.252/1.251
GPC (calibration against BPA polycarbonate): molecular weight Mw=39,681, Mn=12,350, polydispersity D=3.21
Glass transition temperature $T_g$: 173° C.

Example 10

Determination of the water content of polycarbonates:
Water uptake and determination of the water content of polycarbonates from examples 2a), 5a) and 9a) after storage in a damp climate at 95% rh and a storage temperature of 30° C.

The water content is determined after various storage times by means of quantitative Karl-Fischer titration (coulometric titration).
Storage times: 7 days and 14 days
Weathering: damp climate 95% rh and 30° C.
Reproduction: 4 measurements per storage

| Polycarbonate | 7 days [%] | 14 days [%] |
|---|---|---|
| Comparison sample Makrolon CD 2005, Bayer AG | n.d. | 0.32–0.34 |
| 2a) | 0.12/0.15 | 0.15/0.16 |
| 5a) | 0.12/0.14 | 0.12/0.13 |
| 9a) | 0.21/0.23 | 0.20/0.21 |

The comparison with Makrolon CD 2005 a bisphenol A based polycarbonate shows a significantly lower water uptake in the polycarbonates according to the invention.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A compound conforming to formula 1

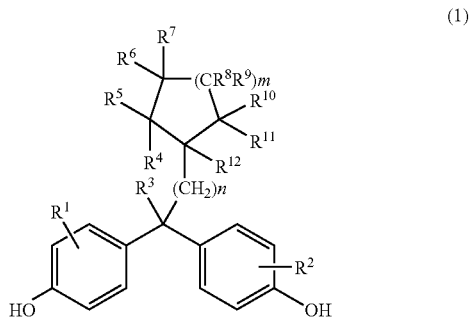

in which
$R^1$ to $R^{12}$ independently one of the other represents hydrogen or $C_1$–$C_{10}$ alkyl radical, n represents an integer of 0 to 10 and m represents an integer of 0 to 10.

2. The compound of claim 1 wherein the radical is linear.

3. The compound of claim 1 wherein the radical is branched.

4. A process for the preparation of the compound of claim 1 comprising condensing in the presence of an acid catalyst at least one corresponding phenol with at least one alkyl-substituted ketone at 0 to 100° C. at a stoichiometric ratio of phenol to ketone of 15 to 1 in the presence of a sulfur-containing compound.

5. A (co)polycarbonate containing structural units derived from the compounds of the formula 1.

6. A molded article comprising the (co)polycarbonate of claim 4.

7. An extruded article comprising the (co)polycarbonate of claim 4.

* * * * *